United States Patent
Theil

(10) Patent No.: US 8,143,372 B2
(45) Date of Patent: Mar. 27, 2012

(54) SYNTHETIC REGULATORS OF FERRITIN PROTEIN NANOCAGE PORES AND METHODS OF USE THEREOF

(75) Inventor: Elizabeth Theil, Oakland, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 925 days.

(21) Appl. No.: 12/122,469

(22) Filed: May 16, 2008

(65) Prior Publication Data

US 2009/0325869 A1    Dec. 31, 2009

Related U.S. Application Data

(60) Provisional application No. 60/939,133, filed on May 21, 2007.

(51) Int. Cl.
*C07K 14/00* (2006.01)
*A61K 38/00* (2006.01)

(52) U.S. Cl. ............................. 530/300; 514/2

(58) Field of Classification Search .................. None
See application file for complete search history.

(56) References Cited

U.S. PATENT DOCUMENTS 7,160,855 B2    1/2007  Theil

OTHER PUBLICATIONS

Barnés et al. Iron uptake in ferritin is blocked by binding of [Cr(TREN)(H(2)O)(OH)](2+), a slow dissociating model for [Fe(H(2)O)(6)](2+). (2002) Proc. Natl. Acad. Sci. USA 99:5195-5200.
Breuer et al. Desferrioxamine-chelatable iron, a component of serum non-transferrin-bound iron, used for assessing chelation therapy. Blood. Feb. 1, 2001;97(3):792-8.
Grossman et al. Unification of the ferritin family of proteins. Proc Natl Acad Sci U S A. Mar. 15, 1992;89(6):2419-23.
Liu et al. Ferritin reactions: direct identification of the site for the diferric peroxide reaction intermediate. Proc Natl Acad Sci U S A. Jun. 8, 2004;101(23):8557-62.
Liu et al. Opening protein pores with chaotropes enhances Fe reduction and chelation of Fe from the ferritin biomineral. Proc Natl Acad Sci U S A. Apr. 1, 2003;100(7):3653-8. Epub Mar. 12, 2003.
Liu et al. Peptides selected for the protein nanocage pores change the rate of iron recovery from the ferritin mineral. J Biol Chem. Nov. 2, 2007;282(44):31821-5.
Ragland et al. Evidence for conservation of ferritin sequences among plants and animals and for a transit peptide in soybean. J Biol Chem. Oct. 25, 1990;265(30):18339-44.
Theil, Elizabeth. Ferritin: at the crossroads of iron and oxygen metabolism.1,2. J Nutr. May 2003;133(5 Suppl 1):1549S-53S.
Torti et al. The molecular cloning and characterization of murine ferritin heavy chain, a tumor necrosis factor-inducible gene. J Biol Chem. Sep. 5, 1988;263(25):12638-44.

*Primary Examiner* — Anand Desai
(74) *Attorney, Agent, or Firm* — Paula A. Borden; Bozicevic, Field & Francis LLP.

(57) ABSTRACT

The present invention provides synthetic regulators of ferritin pores, and compositions comprising the regulators. The regulators function to reduce ferritin demineralization rates. The regulators are useful for treating inflammatory conditions. The present invention also provides methods of treating inflammatory conditions. The present invention further provides synthetic regulators of bacterial mini-ferritins; such regulators are useful as antibacterial agents.

9 Claims, 2 Drawing Sheets

SYNTHETIC REGULATORS OF FERRITIN PROTEIN NANOCAGE PORES AND METHODS OF USE THEREOF

CROSS-REFERENCE

This application claims the benefit of U.S. Provisional Patent Application No. 60/939,133, filed May 21, 2007, which application is incorporated herein by reference in its entirety.

STATEMENT REGARDING FEDERALLY SPONSORED RESEARCH

The U.S. government has certain rights in this invention, pursuant to grant nos. D20251 and AI054193 awarded by the National Institutes of Health.

BACKGROUND

Iron oxy biominerals inside protein nanocages, iron concentrates for protein synthesis and oxygen/peroxide traps for antioxidant protection, are called ferritins. Ferritin is an intracellular protein that concentrates up to 4,500 iron atoms as $Fe_2O_3.H_2O$, and self-assembles from 24 subunits into a hollow protein (usually 12 nm in diameter with an 8 nm-diameter cavity) with 432 symmetry, or in bacteria (Dps or mini-ferritin protein) self-assembles from 12 subunits in a hollow protein (usually 8 nm in diameter with a 5 nm diameter cavity) with 32 symmetry. Ferritin concentrates iron in cells 100 billion times above the solubility of ferric ion in a nontoxic, accessible form. The subunits, four α-helix bundles, contain a catalytic center that converts two Fe(II) atoms to an Fe(III)-oxo bridged dimer intermediate in mineralization. The two classes of ferritins are: i) maxi-ferritins, 24-polypeptide, 4-bundle subunit assemblies found in animals, plants, and bacteria; and ii) mini-ferritins (also called Dsp proteins), 12-polypeptide, 4-bundle subunit assemblies in archaea and bacteria.

In vertebrates, a subunit (L) with an inactive catalytic center coassembles with the catalytically active subunits (H) with tissue-specific H/L ratios to modulate rapid H subunit iron uptake. The H-chain plays an essential role in the rapid biomineralization of iron for storage, while the L-chain serves in iron-core nucleation. In addition to concentrating iron, ferritin plays an important role in scavenging intracellular iron to modulate the cellular labile iron pool. The primary route of iron transit into and out of the protein is through eight hydrophilic pores in the protein shell, which lead to the ferroxidase site (1.0 to 1.5 nm away) and from the ferric oxide nanoparticle (2 nm away). Clusters of glutamate residues located at the subunit dimer interfaces on the ferritin cavity nucleate the mineral.

Reductants and chelators outside the ferritin protein gain access to the ferric mineral inside through pores, controlled by gates, in the ferretin protein nanocages. The ferritin pore gates, identified by mutagenesis and protein crystallography, are highly conserved in both maxi-ferritins and mini-ferritins, and consist of two sets of amino acid pairs: i) between C-D helices, leucine 110/leucine 134; and ii) between the B-C/C-D loops, arginine 71/aspartate 122, in each of three, folded polypeptide, 4-bundle subunits arranged around the pores.

LITERATURE

U.S. Pat. No. 7,160,855; Barnés et al. (2002) Proc. Natl. Acad. Sci. USA 99:5195-5200.

SUMMARY OF THE INVENTION

The present invention provides synthetic regulators of ferritin pores, and compositions comprising the regulators. The regulators function to reduce ferritin demineralization rates. The regulators are useful for treating inflammatory conditions. The present invention also provides methods of treating inflammatory conditions. The present invention further provides synthetic regulators of bacterial mini-ferritins; such regulators are useful as antibacterial agents.

DEFINITIONS

Figure 1:
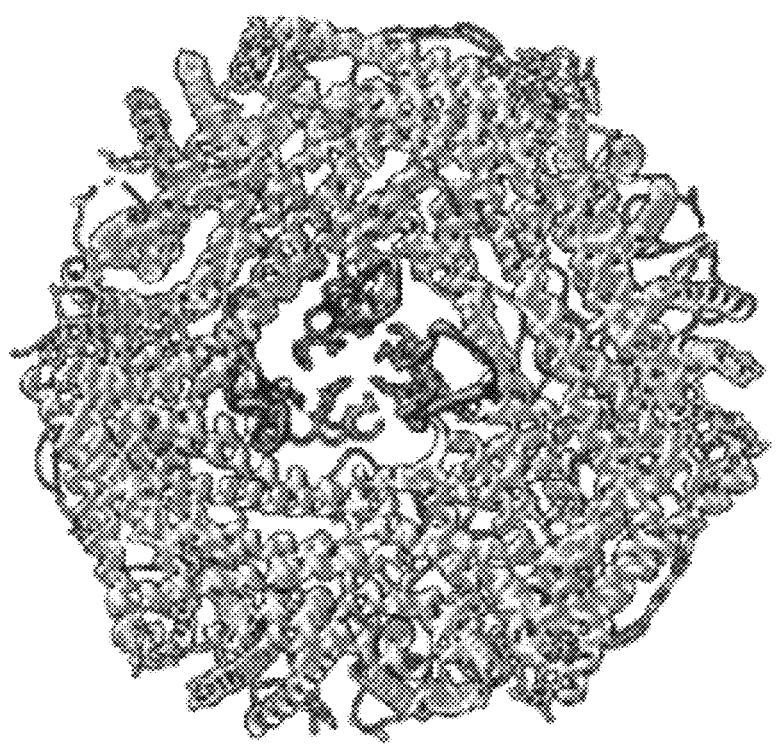
FIG. 1 depicts a ferritin protein nanocage.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, "ferritin" refers to a ferritin protein nanocage comprising mineralized iron, and including H and/or L ferritin polypeptide subunits. "Apoferritin" refers to a ferritin protein nanocage(s) without associated iron. A ferritin protein nanocage can comprises 24 subunits (e.g., a eukaryotic ferritin protein nanocage), or 12 subunits (e.g., a bacterial "mini-ferritin" or Dps protein).

"Purified" as used herein means that the recited material comprises at least about 75%, at least about 80%, or at least about 90% by weight of the total material. As used herein, the term "substantially pure" refers to a compound that is removed from its natural environment or the environment in which it was synthesized, and is at least 60% free, at least 75% free, at least 90% free, at least 95% free, at least 98% free, or at least 99% or more free, from other components with which it is naturally associated or from other components present in a solution in which the compound was synthesized.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and can include: (a) preventing the disease or a symptom of a disease from occurring in a subject which may be predisposed to the disease but has not yet been diagnosed as having it (e.g., including diseases that may be associated with or caused by a primary disease); (b) inhibiting the disease or condition, i.e., arresting its development; and (c) relieving the disease, i.e., causing regression of the disease.

The terms "individual," "host," "subject," and "patient" are used interchangeably herein, and generally refer to a mammal, including, but not limited to, humans; non-human primates such as simians; equines (e.g., horses); canines (e.g., dogs); felines; rodents (e.g., mice; rats); various domesticated livestock (e.g., ungulates, such as swine, pigs, goats, sheep, and the like); as well as domesticated mammalian pets and mammals maintained in zoos. Treatment of humans is of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a synthetic regulator" includes a plurality of such regulators and reference to "the ferritin protein nanocage pore" includes reference to one or more ferritin protein nanocage pores and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides synthetic regulators of ferritin protein nanocage pores, and compositions comprising the regulators. FIG. 1 depicts the ferritin protein nanocages. The view down the 3-fold axis of ferritin shows the pores, folded and unfolded. Ferritin protein nanocage pores unfold independently of the nanocage structure, and are sensitive to temperature, mutation of pore gates, and to physiological urea concentrations. A subject regulator can function to reduce ferritin demineralization rates, e.g., the rate at which iron leaves the ferritin. The regulators are useful for treating inflammatory conditions. For example, regulators of a eukaryotic ferritin nanocage are useful for treating inflammatory conditions, e.g., in a mammal. The present invention also provides methods of treating inflammatory conditions.

The present invention further provides synthetic regulators of bacterial ferritin nanocages. Such regulators are useful as antibacterial agents (e.g., bacteriostatic agents; bacteriocidal agents; etc.). The present invention also provides methods of reducing bacterial cell growth and/or viability.

Synthetic Regulator of Ferritin Protein Nanocage Pores

The present invention provides synthetic regulators of ferritin protein nanocage pores. A subject synthetic regulator reduces the demineralization rate, e.g., a subject synthetic regulator reduces release of iron from ferritin. For example, a subject synthetic regulator reduces the rate of release of iron from a ferritin protein nanocage.

In some embodiments, a subject synthetic regulator reduces the rate of release of iron from both a 24-subunit ferritin protein nanocage and a 12-subunit ferritin protein nanocage. In other embodiments, a subject synthetic regulator preferentially reduces the rate of release of iron from a 24-subunit (e.g., a eukaryotic) ferritin protein nanocage, e.g., in some embodiments, a subject synthetic regulator reduces the rate of release of iron from a 24-subunit (e.g., a eukaryotic) ferritin protein nanocage but does not substantially affect the rate of release of iron from a 12-subunit (e.g., prokaryotic) ferritin protein nanocage. In other embodiments, a subject synthetic regulator reduces the rate of release of iron from a 12-subunit (e.g., a prokaryotic) ferritin protein nanocage but does not substantially affect the rate of release of iron from a 24-subunit (e.g., eukaryotic) ferritin protein nanocage.

For example, a subject synthetic ferritin protein nanocage pore regulator reduces release of iron from ferritin by at least about 5%, at least about 10%, at least about 15%, at least about 20%, at least about 25%, at least about 30%, at least about 40%, at least about 50%, at least about 60%, at least about 70%, or at least about 80%, or more, compared to the release of iron from ferritin in the absence of the regulator.

In some embodiments, a subject ferritin protein nanocage pore regulator increases the amount of iron retained in ferritin as mineralized iron (e.g., increases retention of mineralized iron) by at least about 5%, at least about 10%, at least about 20%, at least about 30%, at least about 40%, at least about 50%, at least about 75%, at least about 2-fold, at least about 2.5-fold, at least about 5-fold, at least about 10-fold, or more than 10-fold, compared to the amount of iron retained in ferritin as mineralized iron in the absence of the regulator.

A subject synthetic ferritin protein nanocage pore regulator binds to one or more amino acids or structures such as helix surfaces in a ferritin protein nanocage pore, and can interfere with unfolding ("opening") of the pore and/or can interfere with access to the ferric mineral contained within the ferritin. For example, a subject synthetic ferritin pore regulator can bind one or more charged amino acid residues around the pore. Examples of charged amino acid residues around a ferritin pore include, but are not limited to, Asp-122 and His-114. Another example is the binding to hydrophobic surfaces or amino acids such as leucine.

Iron release from ferritin can be measured using any convenient method, including methods known in the art. The following is a non-limiting example of a suitable method. In this example, iron release from ferritin is measured by the formation of Fe(II)-bipyridyl. A volume of mineralized ferritin is mixed with an equal volume of a solution of NADH (3 mM), FMN (5 mM) and bipyridyl (5 mM). Formation of Fe(II)-bipyridyl is detected by absorbance at 522 nm. See, e.g., Liu et al. (2003) *Proc. Natl. Acad. Sci. USA* 100:3653-3658. Desferrioxamine can also be used as the chelator.

In some embodiments, the synthetic regulator of ferritin protein nanocage pores comprises a peptide. Suitable peptides can have a length of from about 5 amino acids to about 50 amino acids, e.g., from about 5 amino acids to about 7 amino acids, from about 7 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids. A synthetic regulator that comprises a peptide can include a non-peptide moiety.

Where a synthetic regulator of ferritin pores comprises a peptide, the synthetic regulator can include one or more amino acid residues that bind to a charged amino acid residue or a hydrophobic residue such as leucine. For example, the peptide can include one or more amino acid residues with a charged polar side chain, e.g., one or more amino acids selected from lysine, arginine, histidine, aspartic acid, and glutamic acid. An exemplary peptide comprises the amino acid sequence HHALDGS (SEQ ID NO:1). A peptide comprising the sequence HHALDGS (SEQ ID NO:1) can include one or more additional amino acids on the amino terminus and/or the carboxyl terminus of the HHALDGS (SEQ ID NO:1) sequence. For example, in some embodiments, a synthetic regulator comprises the amino acid sequence HSH-HALDGSGG (SEQ ID NO:2). The peptide can further include one or more amino acids, or a sequence of amino acids, that facilitates entry of the peptide into a cell, e.g, the peptide can include, at the carboxyl terminus and/or at the amino terminus, a sequence of arginine residues. For example, the peptide can include, at the carboxyl terminus and/or at the amino terminus, a sequence of 1, 2, 3, 4, 5, from 5 to 7, from 7 to 9, or from 9 to 12, arginine residues.

Compositions

The present invention provides compositions, including pharmaceutical compositions, comprising a subject synthetic regulator. Compositions comprising a subject synthetic regulator can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like. In some embodiments, a subject composition comprises a substantially pure synthetic regulator of ferritin protein nanocage pores.

A subject synthetic regulator of ferritin protein nanocage pores (referred generically below as an "active agent"; or "drug") can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Identifying Ferritin Pore Regulators

The present invention provides a method of identifying a ferritin protein nanocage pore regulator. The methods generally involve contacting ferritin with a test agent that binds ferritin; and determining the effect (e.g., conducting an assay to determine the effect), if any, of the test agent on the demineralization rate of the ferritin. The present invention further provides a method of identifying a candidate agent for treating an inflammatory disease, the method involving: a) identifying a test agent (e.g., conducting an assay to identify a test agent) that binds ferritin; and b) determining the effect (e.g., conducting an assay to determine the effect), if any, of the ferritin-binding test agent on the rate of release of iron from ferritin, wherein a ferritin-binding test agent that decreases the rate of iron release from the ferritin is considered a candidate agent for treating an inflammatory disease.

Ferritin-binding test agents of interest decrease the rate of iron release from ferritin at least about 5%, at least about 10%, at least about 15%, at least about 20%, at least about 25%, at least about 30%, at least about 40%, at least about 50%, at least about 60%, at least about 70%, or at least about 80%, or more, compared to the rate of release in the absence of the ferritin-binding test agent. For example, a ferritin-binding test agent of interest includes a ferritin-binding test agent that, in the presence of a reductant, decreases the rate of iron release from ferritin at least about 5%, at least about 10%, at least about 15%, at least about 20%, at least about 25%, at least about 30%, at least about 40%, at least about 50%, at least about 60%, at least about 70%, or at least about 80%, or more, compared to the rate of release in the presence of the reductant and in the absence of the ferritin-binding test agent.

Test agents that bind ferritin can be identified by contacting a test agent with ferritin; and determining the ability of the test agent to bind the ferritin. Any of a variety of methods can be used to determine whether a test agent binds ferritin. For example, the ferritin can be immobilized, and a test agent contacted with the immobilized ferritin. A test agent that binds to and forms a complex with the immobilized ferritin is readily detected. As another example, the ferritin can be detectably labeled, and a test agent contacted with the detectably labeled ferritin. Binding of the test agent to the detectably labeled ferritin can be detected by monitoring formation of detectably labeled complexes formed between the bound test agent and the ferritin. One or more washing steps can be included, to remove unbound materials.

The effect of the test agent on demineralization (e.g., on release of iron from ferritin) is generally carried out by contacting the test agent with ferritin in the presence of a reductant and an iron chelating agent such as bipyridyl or desferrioxamine. A suitable reductant comprises nicotinamide adenine dinucleotide reduced form (NADH) and flavin mononucleotide (FMN). The reductant reduces Fe(III) to Fe(II); and the iron chelating agent forms a complex with the Fe(II). Iron release from ferritin can be measured using any convenient method, including methods known in the art. The following is a non-limiting example of a suitable method. In this example, iron release from ferritin is measured by the formation of Fe(II)-bipyridyl. Iron release can be initiated by the addition of 2.5 mM bipyridyl, 2.5 mM FMN, and 2.5 mM NADH to ferritin in 0.1 M MOPS (pH 7.0) and 0.2 M NaCl. Formation of Fe(II)-bipyridyl is detected by measuring absorbance at 522 nm. See, e.g. Liu et al. (2003) *Proc. Natl. Acad. Sci. USA* 100:3653; and Takagi et al. (1998) *J. Biol. Chem.* 273:18685. Desferrioxamine can also be used as an iron chelator. See, e.g., Breuer et al. (2001) *Blood* 97:792.

The ferritin protein nanocage that is used to identify a ferritin-binding test agent, e.g., a ferritin pore-binding test agent, can be any ferritin, where the ferritin can comprise at least a sufficient number of H and/or L subunits to form a particle comprising one or more pores. For example, the ferritin can comprise 12 subunits or 24 subunits. The ferritin subunits that form a ferritin protein nanocage comprising eight or four pores include, but are not limited to, naturally-occurring ferritin subunits, recombinant ferritin subunits, synthetic ferritin subunits, ferritin subunits having a consensus amino acid sequence, and the like.

The ferritin protein nanocage that is used in determining the effect, if any, of a ferritin-binding test agent on the rate of release of iron from ferritin can be any ferritin that binds iron, including a naturally-occurring ferritin, recombinant ferritin, synthetic ferritin, ferritin having a consensus amino acid sequence, and the like. Ferritin H and L subunit amino acid sequences are known in the art. See, e.g., Theil, E. C., in: *Handbook of Metalloproteins*, (Messerschmidt, A. et al., eds.), John Wiley & Sons. The amino acid sequences of ferritin H and L chains of a variety of species are publicly available. For example, amino acid sequences of ferritin H chains are found under the following GenBank accession numbers, where the species is provided in parentheses following the GenBank Accession No.: P02794 (*Homo sapiens*); AAH56858 (*Xenopus laevis*); BAD96181 (*Equus caballus*); AAT11079 (*Rattus norvegicus*); BAD96176 (*Canis familiaris*); BAE78405 (*Felis catus*); and CAA75004 (*Gallus gallus*). Amino acid sequences of ferritin L chains are found under the following GenBank accession numbers, where the species is provided in parentheses following the GenBank Accession No.: P02792 (*Homo sapiens*); AAH60381 (*Xenopus laevis*); BAA03396 (*Equus caballus*); AAH88756 (*Rattus norvegicus*); BAD96179 *Canis familiaris*); and BAE78406 (*Felis catus*). Apoferritin can be mineralized by addition of a solution of ferrous sulfate in a suitable buffered solution (e.g., 0.1 M MOPS and 0.2 M NaCl); and keeping the apoferritin in the ferrous sulfate solution for a suitable period of time and at a suitable temperature (e.g., 2 hours at room temperature and then overnight at 4° C.).

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 and less than about 25,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents can be synthetic peptides of random amino acid sequence. For example, a library (e.g., a phage display library) of synthetic peptides of random amino acid sequence can be contacted with the ferritin protein nanocage. The synthetic peptides can have a length of from about 5 amino acids to about 50 amino acids, e.g., from about 5 amino acids to about 7 amino acids, from about 7 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids.

Assays of the invention include controls, where suitable controls include a sample in the absence of the test agent (e.g., for determining whether a ferritin-binding test agent affects the rate of release of iron from ferritin, a control sample can comprise ferritin, a reductant, and an iron chelating agent, and no test agent). A plurality of assay mixtures can be run in parallel with different agent concentrations to obtain a differential response to the various concentrations. One of these concentrations can serve as a negative control, i.e. at zero concentration or below the level of detection.

Where the screening assay is a binding assay (e.g., to identify an agent that binds the ferritin protein nanocage), one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like buffers, salts, neutral proteins, e.g. albumin, detergents, etc., including agents that facilitate optimal protein-protein binding and/or reduce non-specific or background interactions. Reagents that improve the efficiency of the assay, such as protease inhibitors, anti-microbial agents, etc. may be used. The components of the assay mixture are added in any order that provides for the requisite binding or other activity. Incubations are performed at any suitable temperature, e.g., between 4° C. and 40° C. Incubation periods are selected for optimum activity, but may also be optimized to facilitate rapid high-throughput screening. Typically between 0.1 hour and 1 hour will be sufficient.

Therapeutic Methods

A subject synthetic regulator of a ferritin protein nanocage pore is useful for treating an inflammatory disease or condition. For example, regulators of a eukaryotic ferritin nanocage are useful for treating inflammatory conditions, e.g., in a mammal. Thus, the present invention provides methods of reducing inflammation, and methods of treating an inflammatory disease or condition, the method generally involving administering to an individual in need thereof an effective amount of a subject synthetic regulator. The present invention also provides methods of treating inflammatory conditions.

The present invention further provides synthetic regulators of bacterial ferritin nanocages. Such regulators are useful as antibacterial agents (e.g., bacteriostatic agents; bacteriocidal agents; etc.). The present invention also provides methods of reducing bacterial cell growth and/or viability.

Methods of Reducing Inflammation

The present invention provides methods of reducing inflammation, and methods of treating an inflammatory disease or condition, the method generally involving administering to an individual in need thereof an effective amount of a subject synthetic regulator. In some embodiments, the synthetic regulator reduces the rate of release of iron from both a 24-subunit ferritin protein nanocage and a 12-subunit ferritin protein nanocage. In other embodiments, the synthetic regulator preferentially reduces the rate of release of iron from a 24-subunit (e.g., a eukaryotic) ferritin protein nanocage, e.g., in some embodiments, the synthetic regulator reduces the rate of release of iron from a 24-subunit (e.g., a eukaryotic) ferritin protein nanocage but does not substantially affect the rate of release of iron from a 12-subunit (e.g., prokaryotic) ferritin protein nanocage.

An "effective amount" of a subject synthetic regulator is an amount that, when administered in one or more doses to an individual in need thereof, is effective to reduce inflammation by at least about 10%, at least about 20%, at least about 25%, at least about 30%, at least about 40%, at least about 50%, at least about 60%, at least about 70%, at least about 80%, or at least about 90%, or more, compared to inflammation in the absence of the synthetic regulator.

In some embodiments, an "effective amount" of a subject synthetic regulator is an amount that, when administered in one or more doses to an individual in need thereof, is effective to reduce one or more symptoms or parameters of inflammation by at least about 10%, at least about 20%, at least about 25%, at least about 30%, at least about 40%, at least about 50%, at least about 60%, at least about 70%, at least about 80%, or at least about 90%, or more, compared to the symptom or parameter in the absence of treatment with the synthetic regulator.

For example, where the symptom of inflammation is an elevated level of one or more inflammatory cytokines ("pro-inflammatory cytokines"), an effective amount of a subject synthetic regulator is an amount that, when administered in one or more doses to an individual in need thereof, is effective to reduce the level of the one or more inflammatory cytokines by at least about 10%, at least about 20%, at least about 25%, at least about 30%, at least about 40%, at least about 50%, at least about 60%, at least about 70%, at least about 80%, or at least about 90%, or more, compared to the level of the one or more inflammatory cytokines in the absence of treatment with the synthetic regulator. Pro-inflammatory cytokines include, but are not limited to, TNF-α, IL-1β, IL-6, IFN-α, IFN-β, and IFN-γ.

Inflammatory diseases and conditions that can be treated with a subject method include, but are not limited to, inflammatory bowel disease; systemic lupus erythematosus; rheumatoid arthritis; juvenile chronic arthritis; spondyloarthropathies; systemic sclerosis, e.g., scleroderma; idiopathic inflammatory myopathies such as dermatomyositis, and polymyositis; Sjogren's syndrome; systemic vaculitis; sarcoidosis; autoimmune hemolytic anemia, e.g., immune pancytopenia, paroxysmal nocturnal hemoglobinuria; autoimmune thrombocytopenia, e.g., idiopathic thrombocytopenic purpura, immune-mediated thrombocytopenia; thyroiditis, e.g., Grave's disease, Hashimoto's thyroiditis, juvenile lymphocytic thyroiditis, atrophic thyroiditis; diabetes mellitus, immune-mediated renal disease, e.g., glomerulonephritis, tubulointerstitial nephritis; demyelinating diseases of the central and peripheral nervous systems such as multiple sclerosis, idiopathic polyneuropathy; hepatobiliary diseases such as infectious hepatitis such as hepatitis A, B, C, D, E and other nonhepatotropic viruses; autoimmune chronic active hepatitis; primary biliary cirrhosis; granulomatous hepatitis; sclerosing cholangitis; inflammatory and fibrotic lung diseases (e.g., cystic fibrosis); gluten-sensitive enteropathy; Whipple's disease; autoimmune or immune-mediated skin diseases including bullous skin diseases, erythema multiforme and contact dermatitis, psoriasis; allergic diseases of the lung such as eosinophilic pneumonia, idiopathic pulmonary fibrosis and hypersensitivity pneumonitis; and transplantation associated diseases including graft rejection and graft-versus host disease. In some embodiments, one or more of the aforementioned disorders is specifically excluded. For example, in some embodiments, inflammatory bowel disease is specifically excluded. In embodiments, graft rejection and/or graft versus host disease is specifically excluded.

Methods of Reducing Bacterial Cell Growth and/or Viability

The present invention further provides synthetic regulators of bacterial ferritin nanocages. Such regulators are useful as antibacterial agents (e.g., bacteriostatic agents; bacteriocidal agents; etc.). The present invention also provides methods of reducing bacterial cell growth and/or viability. In some embodiments, the synthetic regulator reduces the rate of release of iron from a 12-subunit (e.g., a prokaryotic) ferritin protein nanocage but does not substantially affect the rate of release of iron from a 24-subunit (e.g., eukaryotic) ferritin protein nanocage.

A subject synthetic ferritin nanocage pore regulator (e.g., synthetic ferritin nanocage pore regulator that preferentially reduces release of iron from a prokaryotic ferritin protein nanocage) inhibits the growth and/or viability of a pathogenic bacterium that produces a Dps protein. Exemplary pathogenic bacteria include, e.g., a pathogenic *Pasteurella* species, a pathogenic *Staphylococci* species, a pathogenic *Streptococcus* species, a pathogenic *Pneumococcus* sp., a pathogenic *Listeria* sp, or any pathogenic bacteria of the genera *Neisseria, Escherichia, Bordetella, Campylobacter, Legionella, Pseudomonas, Shigella, Vibrio, Yersinia, Salmonella, Haemophilus, Brucella, Clostridia, Klebsiella, Francisella, Anthrax, Mycobacterium* sp., *Mycoplasma* sp, *Rickettsia* sp., *Spirochetal* sp., and *Bacterioides*. See, e.g., Schaechter, M, H. Medoff, D. Schlesinger, Mechanisms of Microbial Disease. Williams and Wilkins, Baltimore (1989).

In some embodiments, a subject synthetic ferritin nanocage pore regulator (e.g., synthetic ferritin nanocage pore regulator that preferentially reduces release of iron from a prokaryotic ferritin protein nanocage) inhibits the growth and/or viability of a bacterial bioterror agent, e.g., a bacterial bioterror agent listed by the U.S. Centers for Disease Control and Prevention (CDC). Exemplary bacterial bioterror agents include *Bacillus anthracis, Brucella* sp., *Vibrio cholerae, Coxiella burnetti, E. coli* O157:H7, *Clostridium perfringens, Salmonella* sp., *Shigella* sp., *Francisella tularensis, Yersinia pestis, Burkholderia mallei, Burkholderia pseudomallei, Chlamydophila psittaci, Rickettsia prowazekii*, and the like.

Specific examples of infectious, pathogenic bacteria include but are not limited to: *Helicobacter pyloris, Borelia burgdorferi, Legionella pneumophila, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphthe-*

*riae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israeli*.

"Treating a pathogenic bacterial disease," as used herein, encompasses reducing the number of pathogenic bacteria in the individual (e.g., reducing bacterial load) and/or reducing a parameter associated with the pathogenic bacterial disease, including, but not limited to, reduction of a level of a product produced by the pathogenic bacterium (e.g., a toxin, an antigen, and the like); and reducing an undesired physiological response to the pathogenic bacterium (e.g., fever, tissue edema, and the like).

A subject method of treating a pathogenic bacterial disease generally involves administering to an individual in need thereof (e.g., an individual infected with a pathogenic bacterium) an effective amount of a subject synthetic ferritin nanocage pore regulator (e.g., synthetic ferritin nanocage pore regulator that preferentially reduces release of iron from a prokaryotic ferritin protein nanocage). The methods are effective to treat a pathogenic bacterial disease, e.g., to reduce the number of pathogenic bacteria in the individual and/or to reduce a parameter associated with the disease by at least about 5%, at least about 10%, at least about 20%, at least about 25%, at least about 50%, at least about 75%, at least about 85%, or at least about 90%, up to total eradication of the infecting bacterium and/or an associated parameter, when compared to a suitable control. In an experimental animal system, a suitable control may be a genetically identical animal not treated with the subject synthetic regulator. In non-experimental systems, a suitable control may be the infectious disease present before administering a subject synthetic regulator. Other suitable controls may be a placebo control.

Whether an infectious disease has been treated can be determined in any of a number of ways, including but not limited to, measuring the number of pathogenic bacteria in the individual being treated, using methods standard in the art; measuring a parameter caused by the presence of the pathogenic bacteria in the individual, e.g., measuring the levels of a toxin produced by the pathogenic bacteria; measuring body temperature; measuring the level of any product produced by the pathogen; measuring or assessing any undesired physiological parameter associated with the presence of pathogenic bacteria in an individual. Measuring the number of pathogenic bacteria can be accomplished by any conventional assay, such as those typically used in clinical laboratories, for evaluating numbers of pathogenic bacteria present in a biological sample obtained from an individual. Such methods have been amply described in the literature, including, e.g., *Medical Microbiology* 3rd Ed., (1998) P. R. Murray et al., eds. Mosby-Year Book, Inc. A level of a product, including a toxin, produced by pathogenic bacteria can be measured using conventional immunological assays, using antibody which detects the product, including, but not limited to ELISA, RIA, protein blot assays, and the like. Other suitable assays include in vivo assays for the presence and/or level of bacterial toxins.

Formulations, Dosages, and Routes of Administration

For use in a subject treatment method, a subject synthetic regulator of ferritin protein nanocage pores (referred generically below as an "active agent"; or "drug") can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public In the subject methods, a subject synthetic regulator can be administered to the host using any convenient means capable of resulting in the desired reduction in autoimmune disease. Thus, the synthetic regulator can be incorporated into a variety of formulations for therapeutic administration. More particularly, a subject synthetic regulator can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent may be administered in the form of a pharmaceutically acceptable salt, or an active agent may be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise an active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for an active agent depend on the particular compound employed and the effect to be achieved, and the pharmacodynamics associated with each compound in the host.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, an active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

In general, a subject synthetic regulator is administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

In some embodiments, the amount of a subject synthetic regulator per dose is determined on a per body weight basis. For example, in some embodiments, a subject synthetic regulator is administered in an amount of from about 0.5 mg/kg to about 50 mg/kg, e.g., from about 0.5 mg/kg to about 1 mg/kg, from about 1 mg/kg to about 2 mg/kg, from about 2 mg/kg to about 3 mg/kg, from about 3 mg/kg to about 5 mg/kg, from about 5 mg/kg to about 7 mg/kg, from about 7 mg/kg to about 10 mg/kg, from about 10 mg/kg to about 15 mg/kg, from about 15 mg/kg to about 20 mg/kg, from about 20 mg/kg to about 25 mg/kg, from about 25 mg/kg to about 30 mg/kg, from about 30 mg/kg to about 40 mg/kg, or from about 40 mg/kg to about 50 mg/kg per dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, multiple doses of a subject synthetic regulator are administered. The frequency of administration of a subject synthetic regulator can vary depending on any of a variety of factors, e.g., severity of the symptoms, etc. For example, in some embodiments, a subject synthetic regulator is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a subject synthetic regulator, e.g., the period of time over which a subject synthetic regulator is administered, can vary, depending on any of a variety of factors, e.g., patient response, etc. For example, a subject synthetic regulator can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

A subject synthetic regulator is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. The compound can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Combination Therapies

In some embodiments, a subject treatment method will involve administering an effective amount a subject synthetic regulator and at least one additional anti-inflammatory agent other than a synthetic regulator of ferritin protein nanocage pores.

Suitable anti-inflammatory agents include, but are not limited to, steroidal anti-inflammatory agents, and non-steroidal anti-inflammatory agents.

Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing.

Suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Suitable anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; -Dexamethasone Dipropionate; Diclofenac Potassium; Diclofenac Sodium; Diflorasone Diacetate; -Diflumidone Sodium; Diflunisal; Difluprednate; Diftalone; Dimethyl Sulfoxide; Drocinonide; Endrysone; Enlimomab Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Subjects Suitable for Treatment

Subjects suitable for treatment with a subject method for treating inflammation or treating an inflammatory disease or condition include individuals who have been diagnosed with an inflammatory disease or condition, where inflammatory diseases and conditions include, but are not limited to, systemic lupus erythematosus; rheumatoid arthritis; juvenile chronic arthritis; spondyloarthropathies; systemic sclerosis, e.g., scleroderma; idiopathic inflammatory myopathies such as dermatomyositis, and polymyositis; Sjogren's syndrome; systemic vaculitis; sarcoidosis; autoimmune hemolytic anemia, e.g., immune pancytopenia, paroxysmal nocturnal hemoglobinuria; autoimmune thrombocytopenia, e.g., idiopathic thrombocytopenic purpura, immune-mediated thrombocytopenia; thyroiditis, e.g., Grave's disease, Hashimoto's thyroiditis, juvenile lymphocytic thyroiditis, atrophic thyroiditis; diabetes mellitus, immune-mediated renal disease, e.g., glomerulonephritis, tubulointerstitial nephritis; demyelinating diseases of the central and peripheral nervous systems such as multiple sclerosis, idiopathic polyneuropathy; hepatobiliary diseases such as infectious hepatitis such as hepatitis A, B, C, D, E and other nonhepatotropic viruses; autoimmune chronic active hepatitis; primary biliary cirrhosis; granulomatous hepatitis; sclerosing cholangitis; inflammatory and fibrotic lung diseases (e.g., cystic fibrosis); gluten-sensitive enteropathy; Whipple's disease; autoimmune or immune-mediated skin diseases including bullous skin diseases, erythema multiforme and contact dermatitis, psoriasis; allergic diseases of the lung such as eosinophilic pneumonia, idiopathic pulmonary fibrosis and hypersensitivity pneumonitis; and transplantation associated diseases including graft rejection and graft-versus host disease.

Subjects suitable for treatment with a subject method for treating a bacterial infection include individuals who are infected with a pathogenic *bacterium* that produces a Dps protein, including individual who are infected with a pathogenic *bacterium* and who exhibit one or more symptoms of disease caused by the pathogenic *bacterium*. Subjects suitable for treatment with a subject method for treating a bacterial infection include individuals who are infected with a pathogenic *bacterium*, who have been treated with an antibiotic (e.g., an antibiotic other than a subject synthetic regulator), and who have either failed to respond to the treatment or in whom bacteria resistant to the treatment have grown.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Identification and Characterization of a Peptide Regulator of Ferritin Protein Nanocage Pores The strategy used to identify molecules that would modulate ferritin protein nanocage pore function had two components: (i) searching a combinatorial peptide library for ferritin binding peptides, and (ii) analyzing the effect of reductants on the ferritin mineral inside the protein nanocages. Peptides were selected as the molecules of choice for pore alterations because of the selectivity of urea (1 mM) and guanidine (0.1 mM) in pore unfolding, observed previously. Liu and Theil (2003) *Proc. Natl. Acad. Sci. U.S.A.* 100:3653. Changes in ferritin protein nanocage pore gating can be analyzed as changes in the rate of ferritin iron demineralization, measured as formation of colored Fe chelates, when reductant (NADH/FMN) is added. Jones et al. (1978) *Biochemistry* 17:4011.

Ferritin binding peptides were identified using a phage display, heptapeptide library (New England Biolabs, Ipswich, Mass.). Parmley and Smith (1988) *Gene* 73:305; and Rodi et al. (2002) *Curr. Opin. Chem. Biol.* 6:92. Ferritin H (frog) was used as the adsorbant for the peptides and, once a group of displayed peptides that bound ferritin was isolated (four rounds of selection), peptides that recognized ferritin with unfolded pores were eluted with ferritin H-L134P that had unfolded pores (Takagi et al. (1998) *J. Biol. Chem.* 273: Jin et al. (2001) *Biochemistry* 40:7525; Liu et al. (2003) *Proc. Natl. Acad. Sci. U.S.A.* 100:3653) (peptide group A, n=428). When the DNA sequences encoding the peptides in Group A were translated, the multiple amino acid sequences converged on two peptide sequences: Pep1 (heptapeptide)-NTYYFPK (SEQ ID NO:3) and 2-SHTSPSI (SEQ ID NO:4). Displayed peptides that remained bound to ferritin H after elution with ferritin H-L134P, were then eluted with ferritin H (peptide group B, n=600).

When the DNA sequences encoding the peptides in Group B were translated they converged on three peptide sequences: 3-GDWYLGD (SEQ ID NO:5), Pep4 (heptapeptide)-HHALDGS (SEQ ID NO:1), and 5-HHALGGS (SEQ ID NO:6). The five heptapeptides identified from the phage display library were synthesized as undecapeptides (AnaSpec, Inc., San Jose, Calif.) with two phage coat protein residues at the N-terminus (HS) and two at the C-terminus (GG). Thus, e.g., the undecapeptide form of Pep1 (heptapeptide)-NTYYFPK (SEQ ID NO:3) is HSNTYYFPKGG (SEQ ID NO:7); and the undecapeptide form of Pep4 (heptapeptide)-HHALDGS (SEQ ID NO:1) is HSNHHALDGSGG (SEQ ID NO:2).

The peptides were mixed with wild type ferritin; demineralization was initiated by addition of NADH/FMN, and the appearance of $Fe^{2+}$-bipyridyl measured (FIG. 2). Three of the peptides (2, 3, and 5) had no effect on rates of formation of $Fe^{2+}$-bipyridyl, compared to wild type ferritin H protein nanocages, while Peptide 4 (Group B, eluted with ferritin H protein nanocages, after elution with ferritin H-L134P protein nanocages) decreased the rate 63%. Peptide 4 has 3 His and 1 Asp and could bind to charged residues around the pore. The peptide interaction with ferritin protein nanocage could interfere with unfolding and/or reductant access to the ferric mineral, or might induce conformational changes at the pore or elsewhere.

Peptide 1 (Group A, eluted with ferritin protein nanocage H-L134P) increased rates of ferritin demineralization 3.3-fold, compared to wild type ferritin H (FIG. 2); the rates were similar to the H-L134P pore mutant. Peptide 1, NTYYFPK (SEQ ID NO:3), is very hydrophobic, and may, in analogy to antisense RNA, be an "antisense" peptide that disrupts protein helices.

Figure 2B:
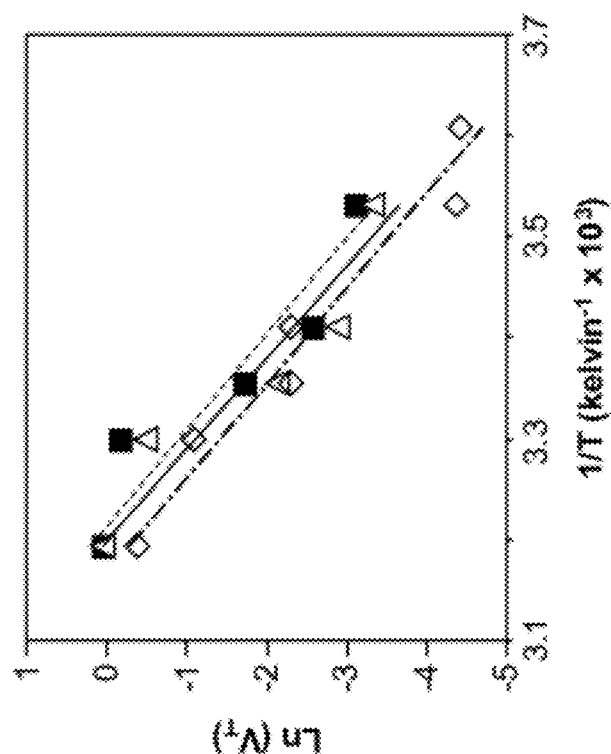
FIGS. 2A and 2B depict the effect of binding peptides on ferritin demineralization.

Temperature effects on the rates of ferritin demineralization are protein dependent (FIG. 2B). In the Arrhenius plot, E‡=86.3 kJ/mole for wild type protein with normally folded pores, and E‡=88.6 kJ/mole for H-L134P protein with unfolded pores. Global thermal stability of the protein nanocage was unaffected by pore mutations. When wild type ferritin was complexed with Peptide 1, E‡ was=87.2 kJ/mole. Such data support the idea that control of the rate of ferritin iron demineralization is related to the unfolding of the pore helix subdomains, which can be increased by hydrophobic binding peptides or by mutation of conserved pore gate residues.

TABLE 1

| Protein | Initial rate of $Fe^{2+}$ bipyridyl formation, pH = 7.0 (mMol) × $10^3 s^{-1}$ | Binding peptide sequence | Rate Change with Temperature (Arrhenius equation) E‡ (kJ/mole) |
|---|---|---|---|
| Wild type H (H-wt) | 1.10 ± 0.13 | (not applicable) | 88.5 ± 2.3 |
| H-wt + Pep1 | 6.80 ± 0.37 | HSNTYYFPKGG (SEQ ID NO: 7) | 79.8 ± 2.6 |
| H-wt + Pep4 | 0.41 ± 0.05 | HSHHALDGSGG (SEQ ID NO: 2) | (not determined) |
| H-L134P; pore gate mutant | 4.03 ± 0.22 | (not applicable) | 77.4 ± 2.1 |

Figure 2A:
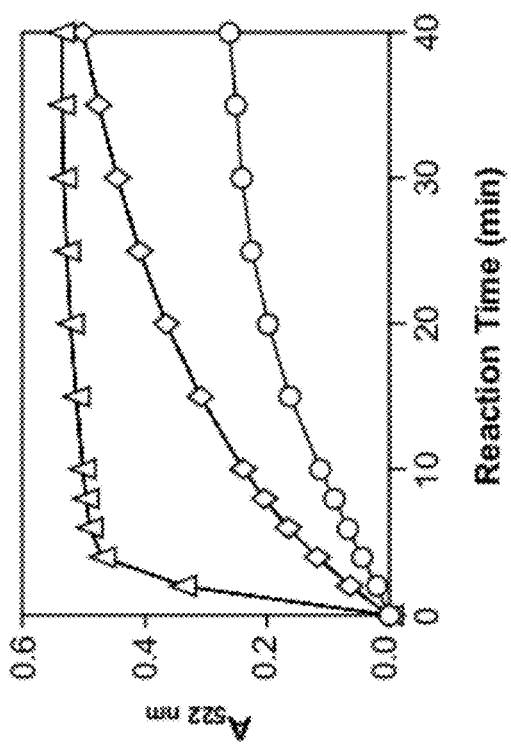

FIG. 2. Effect of binding peptides on removal of iron from the ferritin mineral. Demineralization of ferritin (recombinant, frog ferritin H protein nanocages; protein: 2.06 µM; Fe: 0.99 mM, MOPS: 100 mM, NaCl: 100 mM, pH 7.0) was initiated with reductant (final concentration: 2.5 mM FMN, 2.5 mM NADH), with bipyridyl (2.5 mM); formation of $Fe^{2+}$-bipyridyl was monitored at 522 nm. Initial reaction rates were calculated as described previously (Liu et al. (2003) *Proc. Natl. Acad. Sci. USA* 100:3653). Ferritin binding peptides, identified in a combinatorial, heptapeptide, phage-display library (1.3×10⁹ members, New England Biolabs), were mixed with mineralized ferritin protein nanocages for one hour before initiating demineralization. Peptide 2 (Group A, eluted with H-L134P ferritin protein nanocage) and Peptides 3 and 5 (Group B, eluted with wild type ferritin protein nanocage), had no effect. The data are averages from triplicates in 2-5 independent experiments with two different protein preparations; the error is the standard deviation. FIG. 2A: Progress curves for ferritin protein nanocage H wild type protein+Peptide 1 (Δ), no peptide control (◊), ferritin protein nanocage H wild type protein+Peptide 4 (○) FIG. 2B: comparison of iron demineralization rates for Peptide 1 and ferritin protein nanocage H-L134P pore mutant. Ferritin protein nanocage H wild type protein (◊); ferritin protein nanocage H wild type protein+Peptide 1 (Δ); ferritin protein nanocage H-L134P pore mutant (■).

Example 2

In Vitro Cell-Based Inflammatory Response Assay

Anti-inflammatory activity of a synthetic regulator peptide can be tested in an in vitro cell-based assay. Monocytes such as the THP-1 human monocyte cell line (ATCC TIB-202™; derived from a human leukemia) are used to assess the effect of a synthetic regulator peptide on inflammatory response. Lipopolysaccharide (LPS)-treated THP-1 cell are contacted with a test peptide. The readout for anti-inflammatory activity of a synthetic regulator peptide is a reduction in LPS-induced release of a cytokine such as IL-1β, TNF-α, and IL-6. Cytokine release is measured using an ELISA assay.

For example, a peptide, with or without a poly-Arg tail (e.g., $(Arg)_{11}$; to facilitate cell entry) is contacted with THP-1 cells in culture. Peptides are tested over a concentration range of from about $10^{-4}$M to about $10^{-7}$M.

A reduction in the amount of one or more of IL-1β, TNF-α, and IL-6 in the culture supernatant of LPS-treated monocytes, compared with the amount of the cytokine in LPS-treated monocytes not contacted with the peptide, indicates that the peptide has potential for use as an anti-inflammatory agent.

Example 3

In Vivo Inflammatory Response Assay

Anti-inflammatory activity of a synthetic regulator peptide can be tested in an in vivo non-human animal model of inflammation. Mice (e.g., C57Bl/6 mice) are injected i.p. with: 1) LPS; or 2) LPS+peptide. After a suitable time period (e.g., 4 hours, 6 hours, 12 hours, 24 hours, 2 days, or 3 days), serum levels of IL-1β, TNF-α, and IL-6 are measured. A reduction in the amount of one or more of IL-1β, TNF-α, and IL-6 in serum of (LPS+peptide)-treated mice, compared with the level of the cytokine in serum of LPS-treated mice, indicates that the peptide has potential for use as an anti-inflammatory agent.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A synthetic peptide comprising a ferritin protein nanocage pore-binding moiety, wherein said synthetic peptide has a length of from about 7 amino acids to about 50 amino acids, wherein the peptide comprises the amino acid sequence HHALDGS (SEQ ID NO:1), and wherein said ferritin protein nanocage pore binding moiety reduces the rate of iron release from ferritin.

2. The peptide of claim 1, wherein said peptide has a length of from about 7 amino acids to about 25 amino acids.

3. A pharmaceutical composition comprising:
   a) a synthetic peptide according to claim 1; and
   b) a pharmaceutically acceptable excipient.

4. The composition of claim 3, wherein said composition is an injectable composition.

5. A method of reducing inflammation in an individual, the method comprising administering to the individual an effective amount of a composition of claim 3.

6. The method of claim 5, wherein the inflammation is associated with allergy.

7. The method of claim 5, wherein the inflammation is associated with an autoimmune disorder.

8. The synthetic peptide of claim 1, wherein the synthetic peptide comprises the amino acid sequence HSHHALDGSGG (SEQ ID NO:2).

9. The synthetic peptide of claim 1, wherein the synthetic peptide comprises a sequence of from 1 to 12 arginine residues at the carboxyl and/or amino terminus.

* * * * *

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

His His Ala Leu Asp Gly Ser
1               5

<210> SEQ ID NO 2
<211> LENGTH: 11
<212> TYPE: PRT
<213> ORGANISM: Artificial Sequence
<220> FEATURE:
<223> OTHER INFORMATION: synthetic peptide

<400> SEQUENCE: 2

His Ser His His Ala Leu Asp Gly Ser Gly Gly
1               5                   10

<210> SEQ ID NO 3
<211> LENGTH: 7
<212> TYPE: PRT
<213> ORGANISM: Artificial Sequence
<220> FEATURE:
<223> OTHER INFORMATION: synthetic peptide

<400> SEQUENCE: 3

Asn Thr Tyr Tyr Phe Pro Lys
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Ser His Thr Ser Pro Ser Ile
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Gly Asp Trp Tyr Leu Gly Asp
 1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

His His Ala Leu Gly Gly Ser
 1               5

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

His Ser Asn Thr Tyr Tyr Phe Pro Lys Gly Gly
 1               5                   10
```